United States Patent [19]

Grollier et al.

[11] Patent Number: 5,080,888
[45] Date of Patent: Jan. 14, 1992

[54] COMPOSITION AND PROCESS FOR TREATING KERATINIC SUBSTANCES WITH AT LEAST ONE ANIONIC POLYMER AND AT LEAST ONE QUATERNIZED PROTEIN

[75] Inventors: Jean F. Grollier, Paris; Claude Dubief, Le Chesnay, both of France

[73] Assignee: L'Oreal, Paris, France

[21] Appl. No.: 679,276

[22] Filed: Apr. 2, 1991

Related U.S. Application Data

[62] Division of Ser. No. 284,683, Dec. 15, 1988, Pat. No. 5,008,105, which is a division of Ser. No. 665,386, Oct. 26, 1984, Pat. No. 4,796,646.

[30] Foreign Application Priority Data

Oct. 28, 1983 [LU] Luxembourg .......................... 85.067

[51] Int. Cl.$^5$ .......................... A61K 7/21; A61K 7/04; A61K 7/48
[52] U.S. Cl. ......................................... 424/61; 424/63; 424/47; 424/59; 424/69; 514/773; 514/944; 514/945; 514/937
[58] Field of Search ................... 424/47, 61, 63, 59, 424/69, 78, 81; 514/773, 944, 945, 937

[56] References Cited

U.S. PATENT DOCUMENTS 4,710,374  12/1987  Grollier et al. ...................... 424/61

*Primary Examiner*—Thurman K. Page
*Assistant Examiner*—Susan S. Rucker
*Attorney, Agent, or Firm*—Fleit, Jacobson, Cohn, Price, Holman & Stern

[57] ABSTRACT

Composition and process for treating keratinic substances with at least one anionic polymer and at least one quaternized protein. The invention concerns a process for the cosmetic treatment of keratinic substances and in particular hair, the skin or the nails, wherein at least one strongly cationic quaternized protein and at least one anionic polymer other than homopolymers of acrylic acid crosslinked by means of a polyfunctional agent or an amphoteric polymer are applied on the said substances.

18 Claims, No Drawings

COMPOSITION AND PROCESS FOR TREATING KERATINIC SUBSTANCES WITH AT LEAST ONE ANIONIC POLYMER AND AT LEAST ONE QUATERNIZED PROTEIN

This is a divisional of application Ser. No. 07/284,683, filed on Dec. 15, 1988, which was a divisional of application Ser. No. 06/665,386, filed on Oct. 26, 1984 now U.S. Pat. Nos. 5,008,105 and 4,796,646 respectively.

The present invention relates to new, polymer-based compositions intended to be employed in the treatments of keratinic substances and more particularly in the cosmetic treatment of hair, skin and nails.

Cosmetic treatment is understood to mean all the treatments which make it possible to condition, wash and/or colour keratinic substances such as hair, the skin or the nails.

The Applicant Company has already described in French Patent 2,383,660 compositions based on anionic polymers and on cationic polymers for the treatment of keratinic substances. These compositions make it possible to impart to hair properties of firmness, shape-retention, body, sheen, easy disentangling and pleasant touch.

The quaternised proteins which may be employed according to the invention are known in themselves and have already been recommended for use in cosmetics.

The quaternised proteins more particularly preferred according to the invention are strongly substantive proteins whose substantivity can be compared to cationic polymers containing quaternary ammonium groups such as the water-soluble cyclopolymers mentioned in the Applicant Company's earlier French Patent No. 2,383,660 such as in particular the copolymer of dimethyl diallyl ammonium chloride and acrylamide of molecular weight above 500,000, such as the polymers sold under the name MERQUAT 550 by the MERCK Company.

When these polymers are combined with anionic polymers they impart to the treated hair good disentangling properties and shape-retention and firmness properties.

When they are not combined with the anionic polymer, the quaternised proteins according to the invention impart body and disentanglement, sheen, and pleasant touch to the hair.

The Applicant Company has discovered that their use in combination with anionic polymers such as defined below permitted, in addition to the remarkable properties of disentanglement, body, sheen and touch, to strengthen the shape-retention and firmness properties of hair, which offers an undoubted benefit to the users.

These properties are clearly superior when compared to the properties of the combination of a polymer having a similar substantivity with the same anionic polymer.

A subject of the present invention is thus a process for treating keratinic substances making use of an anionic polymer and a cationic polymer which is a strongly cationic quaternised protein.

Another subject consists of the compositions employed in such a process.

Other subjects will appear from the reading of the description and the examples which follow.

The process for treatment of keratinic substances and preferably cosmetic treatment of hair, the skin and/or the nails, according to the invention, is essentially characterised in that at least one strongly cationic quaternised protein and at least one anionic polymer with the exception of homopolymers of acrylic acid which are crosslinked by means of a polyfunctional agent are applied to the said substance.

The quaternised proteins which are more particularly capable of being employed according to the invention correspond to the formula:

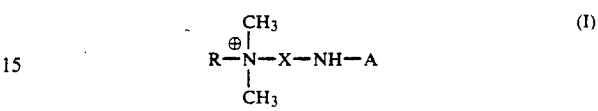

in which A denotes a protein residue derived from hydrolysates of collagen protein, R denotes a lipophile group containing up to 30 carbon atoms and preferably containing 10–20 carbon atoms and namely 12 to 14 carbon atoms, and X denotes an alkylene group containing 1 to 6 carbon atoms.

The preferred quaternised proteins have a molecular weight of between 1,500 and 10,000 and preferably between 2,000 and 5,000.

A more particularly preferred product is the product sold under the name LEXEIN QX-3000 recommended in the CTFA dictionary under the name "Cocotrimonium collagen hydrolysate" and marketed by the Inolex Company.

The anionic polymers which can be employed in the process according to the invention are polymers having a molecular weight of between 500 and approximately 5,000,000 and advantageously between 10,000 and 3,000,000 and have a large number of sulphonic, carboxylic or phosphoric groups. These polymers can also be anionic latices.

The anionic polymers which can be employed in accordance with the invention may be chosen in particular from the polymers derived from a carboxylic or sulphonic acid, mentioned in the Applicant Company's French Patent 2,383,660.

The carboxylic groups are provided in the anionic polymers by unsaturated mono- or dicarboxylic acids denoted particularly by the formula:

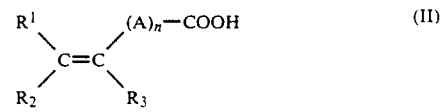

in which n is an integer from 0 to 10, A denotes a methylene group optionally joined to the carbon atom of the unsaturated group or to the adjoining methylene group when n is greater than 1 through the intermediacy of a heteroatom such as oxygen or sulphur, $R_1$ denotes a hydrogen atom or a phenyl or benzyl group, $R_2$ denotes a hydrogen atom or a lower alkyl group or a carboxy group, $R_3$ denotes a hydrogen atom, a lower alkyl group, $-CH_2-$ COOH, phenyl, or benzyl.

In the abovementioned formula a lower alkyl radical denotes preferably a group containing 1 to 4 carbon atoms and in particular methyl, ethyl and the like.

The preferred anionic polymers employed according to the invention are chosen from: - homo- or copolymers of acrylic or metacrylic acid or their salts and in particular the products sold under the names VERSICOL E or K by the Company ALLIED COLLOID, ULTRAHOLD 8 by the Company CIBA GEIGY, the copolymers of acrylic acid and acrylamide sold in the form of their sodium salt under the names RETEN 421, 423 or 425 by the HERCULES Company, sodium polymethacrylate sold under the name DARVAN No. 7 by the Van der Bilt Company, the alkali metal salts of polyhydroxycarboxylic acids sold under the name HYDAGEN F by the HENKEL Company; - copolymers of the abovementioned acids with a monoethylenic monomer such as ethylene, vinylbenzene, vinyl or allyl esters, esters of acrylic or methacrylic acids, optionally grafted on a polyalkylene glycol such as polyethylene glycol and optionally crosslinked. Such polymers are described in particular in French Patent 1,222,944 and German Application 2,330,956; copolymers of this type containing an optionally N-alkylated and/or hydroxyalkylated acrylamide moiety in their chain such as are described in particular in Luxemburg Patents 75,370 and 75,371; acrylic acid homopolymers crosslinked with the aid of a polyfunctional agent such as the group in their chain, and monoesterified or monoamidified, described in French Patents 2,350,834 and 2,357,241 of the Applicant Company.

The polyacrylamide containing carboxylate groups such as those sold by the American Cyanamid Company under the name CYANAMER A 370.

The polymers with a sulphonic group which may be employed in accordance with the invention are chosen in particular from Salts of polystyrenesulphonic acid such as the sodium salts sold under the name Flexan 500 having a molecular weight of approximately 500,000 or under the name Flexan 130 having a molecular weight of approximately 100,000 by the National Starch Company. Such compounds are described in particular in French Patent 2,198,719.

Alkali metal or alkaline earth metal salts of sulphonic acids derived from lignin and, more particularly, calcium or sodium lignosulphonates such as the product sold under the name Marasperse C-21 by the American Can Company and those based on $C_{10}C_{14}$ sold by the Avebene Company.

Sulphonic polyacrylamide salts, such as those mentioned in U.S. Pat. No. 4,128,631 and more particularly polyacrylamidoethylpropanesulphonic acid sold under the name COSMEDIA POLYMER HSP 1180 by the HENKEL Company.

Polymers containing alkylnaphthalenesulphonic acid salt moieties such as the sodium salt sold under the name Darvan No. 1 by the Van der Bilt Company.

Polymers containing at least one vinylsulphonic moiety in their chain such as, more particularly, the polyvinyl sulphonates having a molecular weight of between 1,000 and 100,000 and particularly their sodium, potassium, calcium or ammonium salts and amine salts such as alkylamine or alkanolamine salts, as well as copolymers containing at least vinylsulphonic groups with one or more cosmetically acceptable comonomers such as unsaturated acids chosen from acrylic and methacrylic acids and their esters, amides such as acrylamide or methacrylamide, substituted or unsubstituted, vinyl esters, vinyl ethers and vinylpyrrolidone. These polymers are described more particularly in French Patents 2,238,474 and U.S. Pat. Nos. 2,961,431 and 4,138,477.

It is also possible to employ according to the invention amphoteric polymers in place of the anionic polymers or in combination.

The amphoteric polymers consist of A and B moieties distributed statistically in the polymer chain, where A denotes a moiety derived from a monomer containing at least one basic nitrogen atom and B denotes a moiety derived from an acidic monomer containing one or more carboxylic or sulphonic groups or alternatively A and B can denote groups derived from zwitterionic monomers of carboxybetaines; A and B may also denote a cationic polymer chain containing secondary, tertiary or quaternary amine groups in which chain at least one of the amine groups carries a carboxylic or sulphonic group connected through the intermediacy of a hydrocarbon radical, or else A and B form part of a chain of a polymer containing an $\alpha,\beta$-ethylenedicarboxylate moiety in which one of the carboxylic groups has been caused to react with a polyamine containing one or more primary, secondary or tertiary amine groups.

These polymers are described in particular in U.S. Pat. Nos. 3,836,537 and French Patent 1,400,366, as well as in French Patent Publication 79/29,319. It is also possible to employ amphoteric polymers of dialkylaminoalkyl (meth)acrylate or betainised (methy)acrylamide containing the moieties:

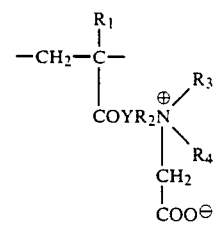

in which $R_1$ denotes a hydrogen atom or a methyl group, $R_2$ denotes an alkylene group containing 1 to 4 carbon atoms, Y denotes O or NH, $R_3$ and $R_4$ denote independently of each other hydrogen, alkyl containing 1 to 4 carbon atoms, the copolymers with acrylic or methacrylic acid esters containing alkyl radicals having 4 to 24 carbon atoms and acrylic or methacrylic acid esters containing alkyl radicals having 1 to 3 carbon atoms and optionally other monomers such as N-vinylpyrrolidone, acrylamide, hydroxyethyl or propyl acrylate or methacrylate, acrylonitrile, styrene, chlorostyrene, vinyltoluene, vinyl acetate, and the like, which are known in themselves.

It is also possible to employ in accordance with the invention anionic latices which are latices whose anionic functional groups are provided either by polymerisation or copolymerisation of anionic monomers by the usual processes known to those skilled in the art, either by combination of the anionic free radical originating from the reaction initiator with the monomer or the monomers in question during the initiation of polymerisation of the said monomers or by juxtaposition of these two processes for synthesis or alternatively by introducing end groups by a chain transfer reaction in the second process making use of a reaction initiator.

The process making use of reaction initiators is described in particular in the article by R. M. FITCH "Preparation and characterisation of charge stabilized polymer colloids" in "Polyelectrolytes and their applications", 51–69 by D. REIDER Publishing Company.

The latices employed more particularly according to the invention result from the polymerisation of various monomers such as styrene, butadiene, acrylonitrile, chloroprene, vinylidene chloride, isoprene, isobutylene, vinyl chloride, and esters of acrylic, methacrylic, vinyl acetic, maleic, crotonic or itaconic acids, employed alone or in a mixture with one or more of the following ion-forming monomers:

acrylic, methacrylic, itaconic, maleic, crotonic, para-styrenesulphonic, vinylsulphonic, 2-methacryloyloxyethylsulphonic and 2-acrylamido-2-methylpropylsulphonic acids.

The latices may also be obtained by polymerisation or copolymerisation of the abovementioned ion-forming monomers.

The latices obtained according to the abovementioned second process result from the use of initiators chosen from redox systems, peroxides, perphosphates, percarbonates, persulphates, peroxidised organic acids such as for example peracetic acid, or the persulphate-bisulphate-iron mixture.

The functional monomers employed in the case of chain transfer reaction are chosen from organic thio-acids such as for example mercaptoacetic acid.

Among the anionic latices which may be employed in accordance with the invention particular mention can be made of the products sold under the following tradenames: KARAMUL 142 ST sold by the FRANCONYX Company which is an acrylic emulsion; the latices sold under the names PRIMAL B52, PRIMAL K3, PRIMAL TR 485, PRIMAL AS 95 consisting of acrylic aqueous emulsions sold by the ROHM & HAAS Company, containing between 20 and 50% solids; APPRETAN ANT which is a dispersion of an acrylic copolymer, sold by the HOECHST Company; ACRYMUL AM 176 R which is an aqueous emulsion of an acrylic copolymer containing reactive groups, sold by the PROTEX Company; NATIONAL 125 4477 and 125 4445 which are aqueous dispersions of an acrylic copolymer, NATIONAL 125 2833, NATIONAL 125 2869, NATIONAL 125 2873 which are emulsions of a vinyl acetate/acrylic acid copolymer sold by the NATIONAL ADHESIVES & RESINS Company; LUCIDENE 347 which is a styrene acrylic acid emulsion, sold by the WILLIAMS Company; SYNTRAN 1026 which is an acrylic acid-ethylene-styrene emulsion sold by the INTER POLYMER CORPORATION; COLAPERLE SPA which is an aqueous dispersion of an acrylic copolymer sold by the PCUK Company; a CHEMIGUM LATEX 6271 which is a copolymer of carboxylated butadiene and acrylonitrile sold by the GOODYEAR Company.

It is self-evident that other anionic latices may be employed in accordance with the invention.

The anionic polymers which are more particularly preferred are those containing a linear uncrosslinked acrylic or methacrylic moiety, a maleic anhydride moiety optionally monoesterified or hydrolysed or a grafted crotonic acid moiety optionally crosslinked or incorporating more than one monomer other than vinyl acetate.

The polymers are employed in accordance with the invention either according to a two-step process including in a first stage the application of a composition containing the quaternised protein and in a second stage the application of a composition containing the anionic polymer such as defined above, or including in a first stage the application of a composition containing the anionic polymer and in a second stage the application of a composition containing the quaternised protein, or by means of a single composition containing, in a solvent medium, the anionic polymer and the quaternised protein.

The compositions employed for applying the polymer or polymers on the keratinic fibres are compositions containing the said polymers in concentrations from 0.01 to 10% by weight and preferably in concentrations of between 0.1 and 5% by weight in a suitable medium for their application on these fibres. The pH of these compositions is generally between 2 and 11 and preferably between 3 and 10.

It may be adjusted with alkalising or acidifying agents which are known in themselves.

These compositions may be in various forms such as liquid, cream, emulsion, gel, thickened lotion, or powder; they may contain water as well as any cosmetically acceptable solvent chosen, in particular, from monoalcohols, such as alcanols containing 1 to 8 carbon atoms, such as ethanol, isopropanol, benzyl alcohol, phenylethyl alcohol, polyalcohols such as alkylene glycols, such as ethylene glycol, propylene glycol, glycol ethers such as mono-, di- and triethylene glycol monoalkyl ethers such as for example ethylene glycol monomethyl ether, ethylene glycol monoethyl ether, diethylene glycol monoethyl ether, employed alone or as a mixture. These solvents are present in concentrations below or equal to 70% by weight relative to the weight of the total composition.

These compositions may also be packaged as aerosol and in that case applied in the form of an aerosol spray, or in the form of aerosol foam.

In this form of embodiment it is possible to employ in particular, as propellant gas, carbon dioxide, nitrogen, nitrogen oxide, volatile hydrocarbons such as butane, isobutane and propane and preferably chlorine-containing and fluorine-containing hydrocarbons.

Preferred compositions may also contain electrolytes such as alkali metal salts, such as sodium, potassium or lithium salts, these salts being preferably chosen from sulphates, halides, such as chloride, bromide or salts of organic acids such as acetates or lactates, as well as alkaline-earth metal salts chosen preferably from calcium, magnesium or strontium carbonates, silicates, nitrates, acetates, gluconates, pantothenates, and lactates.

These compositions may also be in the form of powder or of lyophilysates to be diluted before use.

The compositions according to the invention may contain any other ingredient usually employed in cosmetics, such as perfumes, colorants whose function may be to colour the composition itself or the fibres, preserving agents, sequestering agents, thickeners, silicones, softening agents, foam synergists, foam stabilisers, sunscreens, peptising agents, and anionic, nonionic, cationic or amphoteric surface-active agents or their mixtures.

These compositions may be employed in particular in the form of shampoo, rinse lotion, cream or treatment product which can be applied before or after dyeing or bleaching, before or after shampooing, before or after permanent waving or hair straightening and can also have the form of a colouring product and hair setting lotion, blow-drying lotion, or product for bleaching, permanent waving or hair straightening.

These compositions are applied preferably on the hair and the nails where the best results are found.

A particularly preferred embodiment consists of the use in the form of shampoo for washing hair.

In this case, these compositions contain anionic, cationic, nonionic or amphoteric surfactants or their mixtures in a concentration of between 3 and 50% by weight, preferably between 3 and 20% and their pH is between 3 and 10.

A list of the surfactants which may be employed in accordance with the invention is given in the Applicant Company's French Patent 2,383,660.

Another preferred embodiment consists of the use in the form of rinse lotion to be applied mainly before or after shampooing. These lotions may be aqueous or aqueous alcoholic solutions, emulsions or thickened lotions or gels. When the compositions are in the form of emulsions they may be nonionic or anionic. The nonionic emulsions consist chiefly of a mixture of oil and/or fatty alcohol and polyethoxylated alcohol such as polyethoxylated stearyl or cetylstearyl alcohols and cationic surfactants may be added to these compositions.

An embodiment which is also preferred and which gives advantageous results on hair consists of the compositions such as defined above, pressurised in an aerosol device and forming a foam when exposed to air.

The anionic emulsions are formed essentially starting from soap.

When the compositions are in the form of thickened lotion or gel, they contain thickeners in the presence or absence of solvent. The thickeners which may particularly be employed are especially sodium alginates, gum arabic, cellulose derivatives and it is also possible to obtain thickening with a mixture of polyethylene glycol and polyethylene glycol stearate or distearate or with a mixture of phosphoric ester and amide. The concentration of thickener may vary between 0.05 and 15% by weight.

When the compositions are in the form of hair-dressing lotion, hair-shaping lotion or hairsetting lotion, they generally incorporate the polymers defined above, as well as nonionic polymers if appropriate, in aqueous, alcoholic or aqueous alcoholic solution.

When the compositions of the invention are intended to be employed for dyeing keratinic fibres and in particular human hair, they contain, in addition to the quaternised protein or proteins and the anionic polymer, at least one precursor of an oxidation dye and/or a direct dye. They may also contain any other adjuvant usually employed in this type of composition.

The pH of the dyeing compositions is generally between 7 and 11 and can be controlled at the desired value by adding an alkalising agent.

The composition according to the invention may also be employed for waving or straightening hair. In this case, the composition contains, in addition to the anionic polymer or polymers and the cationic protein, one or more reducing agents, and optionally other adjuvants usually employed in this type of composition. These compositions are intended to be employed in conjunction with an oxidising composition.

When the polymers are applied according to a two-step process, the combination of the quaternised protein with the anionic polymer is produced directly in the region of the fibres.

This process can be employed by applying in a first stage a composition in the form of pre-lotion containing the quaternised protein and in a second stage a composition such as for example a shampoo or a dye containing the anionic polymers defined above.

According to another alternative form of the invention, a shampoo containing the quaternised protein can be applied in a first stage and a composition such as a lotion containing the anionic polymer in a second stage.

It is also possible to proceed by employing in succession a composition for permanent waving, hair straightening, colouring, or bleaching containing the quaternised protein and to follow this first treatment with a second treatment with a composition containing the anionic polymer, the latter being put in a composition which may be a shampoo or a simple lotion or alternatively an oxidising solution, particularly in the case of the permanent waving or colouring compositions.

It is also possible to employ in a first stage a shampoo containing the quaternised protein and in a second stage another shampoo containing the anionic polymer, the pH of the compositions applied in these two stages being capable of being different and adjusted so as to be present at the time of the application of the composition containing the anionic polymer under conditions which permit a good deposit of the combination according to the invention on the fibres to be treated.

The following examples are intended to illustrate the invention without, however, being of a limiting nature.

EXAMPLE 1

A shampoo of the following composition is prepared:

| | |
|---|---|
| Lexein QX 3000 | 1.2 g AI |
| Polacrylic acid of approximate molecular weight 3500 sold in 25% strength as AI in water by the ALLIED COLLOIDS Company under the name VERSICOL E5 | 0.6 g AI |
| Sodium alkyl ($C_{12}$-$C_{14}$) ether sulphate oxyethylenated with 2.2 moles of ethylene oxide and 25% of active ingredient | 8 g AI |
| Water, perfume, preserving agent, colorant q.s. | 100 g |

The pH is adjusted to 7.5 with sodium hydroxide.

Hair washed with the aid of this shampoo has, once dried, good settability as shown by a firmer hairstyle and good shape retention with time.

EXAMPLE 2

A shampoo with the following composition is prepared:

| | |
|---|---|
| Lexein QX 3000 | 3 g AI |
| Surfactant of formula:<br>R—CHOH—CH$_2$—O—(CH$_2$—CHOH—CH$_2$—O)$_n$H<br>R: mixture of $C_9$-$C_{12}$ alkyl radicals<br>n: denotes a statistical average value of approximately 3.5 | 4 g AI |
| Nonionic surfactant based on polyglycerolated (4.2 moles) lauryl alcohol in solution containing approximately 60% active ingredient | 6 g AI |
| Polymethacrylic acid of approximate molecular weight 26,000 sold at 20% AI in water under the name VERSICOL K13 by the ALLIED COLLOIDS Company | 0.2 g AI |
| Sodium chloride | 4 g |
| Water, perfume, colorant, preserving | 100 g |

-continued

| | |
|---|---|
| agent q.s. | |

The pH is adjusted to 6.7 with sodium hydroxide.

Hair washed with the aid of this shampoo has good settability as shown by a firmer hairstyle and good shape retention with time.

EXAMPLE 3

A shampoo of the following composition is prepared:

| | |
|---|---|
| Lexein QX 3000 | 4.5 g AI |
| Triethanolamine alkyl ($C_{12}$-$C_{14}$) sulphate containing 40% active ingredient | 10 g AI |
| Surfactant of formula: | 2 g AI |

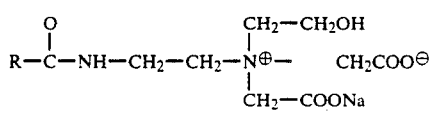

| | |
|---|---|
| with R—CO copra fatty acid radical sold under the name MIRANOL C2M conc. by the MIRANOL Company | |
| Copolymer of acrylic acid/methacrylic acid and a monomer consisting of one of their simple esters sold under the name Ultra hold 8 by the CIBA GEIGY Company | 0.15 g AI |
| Sodium chloride | 4 g |
| Water, perfume, colorant, preserving agent q.s. | 100 g |

The pH is adjusted to 7.3 with sodium hydroxide.

Hair washed with the air of this shampoo has good settability as shown by a firmer hairstyle and good shape retention with time.

EXAMPLE 4

A shampoo of the following composition is prepared:

| | |
|---|---|
| Lexein QX 3000 | 2.5 g AI |
| Methyl vinyl ether copolymer with maleic anhydride monoesterified with butanol, sold t 50% concentration of active ingredient in ethanol under the name GANTREZ ES 425 by the G.A.F. Company | 0.3 g AI |
| Sorbitan monolaurate polyoxyethylenated with 20 moles of ethylene oxide | 5 g AI |
| Sodium and magnesium lauryl ether sulphate containing 30% of active ingredient, sold under the name TEXAPON ASV by HENKEL Company | 7.5 g AI |
| Water, perfume, colorant, preserving agent q.s. | 100 g |

The pH is adjusted to 7 with sodium hydroxide.

Hair washed with the aid of this shampoo has good settability as shown by a firm hairstyle and good shape retention with time.

EXAMPLE 5

A shampoo of the following composition is prepared:

| | |
|---|---|
| Lexein QX 3000 | 1 g AI |
| 7-Trideceth carboxylic acid of formula: | |
| $CH_3(CH_2)_{11}CH_2$—(O $CH_2$-$CH_2$)$_6$O—$CH_2$—COOH containing 90% of active ingredient, sold under the name SANDOPAN DTC acid by the SANDOZ Company | 5 g AI |
| Sodium hemisulphosuccinate of polyethoxylated lauryl alcohol containing 40% of active ingredient, sold under the name SETACIN 103 special by the ZSCHIMMER and SCHWARZ Company | 14 g AI |
| Sodium chloride | 4 g |
| Polyacrylic acid of approximate molecular weight 27,000 sold at 25% of active ingredient under the name VERSICOL E7 by the ALLIED COLLOIDS Company | 0.8 g AI |
| Water, perfume, colorant, preserving agent q.s. | 100 g |

The pH is adjusted to 6.3 with sodium hydroxide.

Hair washed with the aid of this shampoo has good settability as shown by firm hairstyle and good shape retention with time.

EXAMPLE 6

A rinse lotion with the following composition is prepared:

| | |
|---|---|
| Lexein QX 3000 | 0.7 g AI |
| Na polyvinylsulphonate | 0.4 g AI |
| NaCl | 7 g |
| Water, perfume, colorant, preserving agent q.s. | 100 g |

The pH is adjusted to 7.2 with sodium hydroxide.

Hair is washed with the aid of a conventional shampoo: rinsed with the aid of this composition, it has good settability after being dried.

EXAMPLE 7

An after-shampoo is prepared in the form of aerosol foam with the following composition:

| | |
|---|---|
| Lexein QX 3000 | 5 g AI |
| Methyl vinyl ether/maleic anhydride copolymer sold under the name GANTREZ AN 119 by the G.A.F. Company and employed in the form of sodium salt | 0.9 g as AI of the acid form |
| Sodium chloride | 4 g |
| Distearyl dimethylammonium chloride | 0.4 g |
| Water, perfume, colorant, preserving agent q.s. | 100 g |

The pH is adjusted to 7.4 with sodium hydroxide.

Schedule for filling the aerosol can:

| | |
|---|---|
| Composition 7 | 90 g% |
| Propellant Freon 114 (43)/ Freon 12 (57) | 10 g% |
| | 100 g |

Hair treated with the aid of this composition has good settability as shown by a firmer hairstyle and good shape retention with time.

EXAMPLE 8

An after-shampoo having the following composition is prepared:

| | |
|---|---|
| Lexein QX 3000 | 2 g AI |
| Polyacrylic acid sold at 50% active ingredient under the name GOODRITE K 732 by the GOODRICH Company | 1.6 g AI |
| Mixture of cetylstearyl alcohol and | 5 g AI |

| | |
|---|---|
| cetylstearyl alcohol oxyethylenated with 15 moles of ethylene oxide, sold under the name Sinnowax AO by the HENKEL Company | |
| Hydroxyethylcellulose sold under the name CELLOSIZE QP4400H by the UNION CARBIDE Company | 0.5 g AI |
| Stearyldimethyl benzylammonium chloride | 0.8 g AI |
| Sodium chloride | 4 g |
| Water, perfume, colorant, preserving agent q.s. | 100 g |

The pH is adjusted to 5 with sodium hydroxide.

Hair washed with the aid of this shampoo has good settability as shown by a firmer hairstyle and good shape retention with time.

EXAMPLE 9

A shampoo with the following composition is prepared:

| | |
|---|---|
| Lexein QX 3000 | 1.5 g AI |
| Sodium chloride | 4 g |
| Partially hydrolysed polyacrylamide of approximate moleqular weight 200,000, specific viscosity 3.7 ± 0.5 sold under the name CYNAMER A.370 by the AMERICAN CYANAMID Company | 0.6 g AI |
| Sodium and magnesium lauryl ether sulphate sold at 30% of active ingredient under the name TEXAPON ASV by the HENKEL Company | 10 g AI |
| pH adjusted to 7.8 with sodium hydroxide | |
| Perfume, preserving agent, q.s. | |
| Water q.s. | 100 g |

EXAMPLE 10

A shampoo of the following composition is prepared:

| | |
|---|---|
| Lexein QX 3000 | 1.2 g AI |
| Sodium chloride | 4.0 g |
| Vinyl acetate/crotonic acid/vinyl neo-decanoate terpolymer sold by the NATIONAL STARCH Company under the name RESINE 28.29.30 neutralised with NaOH | 0.6 g AI |
| Surfactant of formula: R—CHOH—CH$_2$—O—(CH$_2$—CHOH—CH$_2$O—)$_n$H with R: mixture of C$_9$-C$_{12}$ alkyl radicals n: statistical value of 3.5 | 6.0 g AI |
| Triethanolamine alkyl sulphate | 3.0 g |
| pH adjusted to 8.3 with NaOH | |
| Perfume, preserving agent q.s. | |
| Water q.s. | 100 g |

EXAMPLE 11

An after-shampoo of the following composition is prepared:

| | |
|---|---|
| Lexein QX 3000 | 0.8 g AI |
| Sodium chloride | 4.0 g |
| Aqueous dispersion of an acrylic co-polymer sold at 25% of active ingredient under the name NATIONAL 125 2813 by the NATIONAL ADHESIVE & RESINS Company | 0.4 g AI |
| Mixture of cetylstearyl alcohol and cetylstearyl alcohol oxyethylenated with 15 moles of ethylene oxide, sold under | 5.0 g AI |
| the name "SINNOWAX AO" by the HENKEL Company | |
| Stearyldimethylbenzyl ammonium chloride | 0.8 g |
| Hydroxyethylcellulose sold under the name "CELLOSIZE QP 4400 H" by the UNION CARBIDE Company | 0.5 g |
| pH adjusted to 5.6 with HCl | |
| Perfume, colorant, preserving agent q.s. | |
| Water q.s. | 100.0 g |

EXAMPLE 12

An after-shampoo with the following composition is prepared:

| | |
|---|---|
| Lexein QX 3000 | 2.0 g AI |
| Vinyl acetate/crotonic acid/vinyl neo-decanoate terpolymer sold by the NATIONAL STARCH Company under the name RESINE 28.29.30, neutralised | 0.7 g AI |
| Cetyl alcohol | 3.0 g |
| Polawax GP 200 | 1.5 g |
| Distearyldimethylammonium chloride | 0.9 g |
| Sodium chloride | .4 g |
| pH adjusted to 7.8 with HCl | |
| Perfume, colorant, preserving agent q.s. | |
| Water q.s. | 100 g |

EXAMPLE 13

A lotion with the following composition is prepared:

| | |
|---|---|
| Terpolymer of vinyl acetate, crotonic acid and polyethylene glycol, sold by the HOECHST Company under the name ARISTOFLEX A | 1 g AI |
| Lexein QX 3000 | 0.25 g AI |
| Ethyl alcohol q.s. | 20° |
| pH 8 with 2-amino- 2-methyl-1-propanol | |
| Perfume, colorant, preserving agent q.s. | |
| Water q.s. | 100 g |

This composition is applied on washed hair which is shaped and dried without having been rinsed after application of the composition.

EXAMPLE 14

A foam with the following composition is prepared:

| | |
|---|---|
| Copolymer of methyl vinyl ether with maleic anhydride monoesterified with butanol, sold at 50% of active ingredient in ethanol under the name GANTREZ ES 425 by the GENERAL ANILIN Company | 1 g AI |
| Quaternised protein sold at 30% of active ingredient under the name LEXEIN QX 3000 by the INOLEX Company | 0.5 g AI |
| pH 7.5 with 2-amino-2-methyl-1-propanol | |
| Perfume, colorant, preserving agent q.s. | |
| Water q.s. | 100 g |

This composition is packaged in an aerosol device.

| | |
|---|---|
| Active principal: | 90 g |
| Propellants: Freons 12/114 (50/50 by weight): | 10 g |
| Total | 100 g |

The foam is applied to clean hair.

After shaping and drying, the hair shows good shape retention.

EXAMPLE 15

The following composition is prepared:

| | |
|---|---|
| Lexein QX 3000 | 0.4 g AI |
| Copolymer of methyl vinyl ether with maleic anhydride monoesterified with butanol, sold at 50% concentration of active ingredient in ethanol under the name GANTREZ ES 425 by the G.A.F. Company and 20% neutralised with 2-amino-2-methyl-1-propanol pH adjusted to 8 with 2-amino-2-methyl-1-propanol | 0.8 g AI |
| Water q.s. | 100 g |

This composition is applied on nails as a hardener.

We claim:

1. A composition for the cosmetic treatment of nails and skin, comprising, in a cosmetically acceptable medium which is suitable for application to said nails or skin a strongly cationic quaternized protein and an anionic latex, or an amphoteric polymer wherein:

the anionic functional groups of said anionic latex are produced either by polymerization or copolymerization of anionic monomers in which polymerization or copolymerization is effected either by combination of an anionic free radical originating from the reaction initiator with the monomer or the monomers during the initiation of polymerisation of said monomers or by juxtaposition of these two processes of synthesis or, alternatively, by the introduction of end groups by a chain transfer reaction in the second process employing a reaction initiator;

said strongly cationic quanternized protein has the formula:

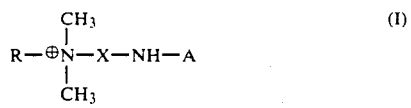

$$R-\overset{\oplus}{\underset{\underset{CH_3}{|}}{\overset{\overset{CH_3}{|}}{N}}}-X-NH-A \quad (I)$$

in which A is a protein residue derived from hydrolysates of collagen protein, R is a lipophilic group containing up to 30 carbon atoms, and X is an alkylene group containing from 1 to 6 carbon atoms;

said amphoteric polymer contains two moieties, moiety A and moiety B, which are distributed statistically in said amphoteric polymer chain such that moiety A is derived from a monomer that contains at least one basic nitrogen atom and moiety B is derived from an acidic monomer that contains at least one carboxylic or sulphonic group, or moieties A and B are groups that are derived from zwitterionic monomers of carboxybetaines or are cationic polymer chains that contain secondary, tertiary or quaternary amine groups such that at least one of said amine groups includes a carboxylic or sulphonic group connected to said amine group via a hydrocarbon radical, or moieties A and B form part of a chain of a polymer that contains an α,β-ethylenedicarboxylate moiety in which one of the carboxylic groups has reacted with a polyamine that contains one or more primary, secondary, or tertiary amine groups; and, the concentration of said strongly cationic quaternized protein and said anionic latex or amphoteric polymer is between 0.01 and 10% by weight.

2. The composition of claim 1, wherein the molecular weight of the quaternized protein is between 1,500 and 10,000.

3. The composition of claim 1, wherein the anionic functional groups of the anionic latex are produced by polymerization of a monomer selected from the group consisting of styrene, butadiene, acrylonitrile, chloroprene, vinylidene chloride, isoprene, isobutylene, vinyl chloride and esters of acrylic methacrylic, vinyl acetic, maleic, crotonic, or itaconic acid, wherein said monomer is polymerized alone or as a mixture with one or more of the ion-forming monomers selected from the group consisting of acrylic, methacrylic, itaconic, maleic, crotonic, para-styrenesulphonic, vinylsulphonic, 2-methacryloyloxyethylsulphonic and 2-acrylamido-2-methylpropylsulphonic acids.

4. The composition of claim 1, further comprising electrolytes selected from the group consisting of alkali metal salts and alkaline earth metal salts.

5. The composition of claim 1, wherein the pH is between 2 and 11.

6. A composition of claim 1, that is formulated as a liquid, creams, emulsion, gel, thickened lotion or powder.

7. A composition of claim 1, that contains water or a mixture of water and a cosmetically acceptable solvent selected from the group consisting of monoalcohols containing 1 to 8 carbon atoms, polyalcohols, glycol ethers and mixtures of said monoalcohols, polyalcohols, and glycol ethers.

8. A composition of claim 1, that is formulated as powder or lyophilizate that is diluted before use.

9. The composition of claim 1, further comprising perfumes, colorants for coloring the composition, colorants for coloring the nails or skin, preservatives, sequestering agents, thickeners, silicone, softening agents, foam synergists, foam stabilizers, sunscreening agents, peptising agents, anionic, nonionic, cationic or amphoteric surface-active agents or mixtures of said surface active agents.

10. A composition of claim 1, which is formulated as a thickened lotion or gel, further comprising thickeners selected from the group consisting of sodium alginates, gum arabic, cellulose derivatives, mixtures of polyethylene glycol and polyethylene glycol stearate or distearate and mixtures of phosphoric ester and amide, wherein the concentration of thickener is between 0.05 and 15% by weight relative to the total weight of the composition.

11. The composition of claim 1, wherein the concentrations of the quaternized proteins and of the anionic latex are between 0.01 and 10% by weight.

12. The composition of claim 11, wherein said concentrations are between 0.1 and 5%.

13. A composition of claim 1 that is packaged as an aerosol that is formulated as a spray or foam.

14. A composition of claim 13 that is formulated as an aerosol that forms a foam upon expansion in the air.

15. A process for hardening nails, comprising applying a composition of claim 1 on the nails.

16. A process for the cosmetic treatment of the skin and nails, comprising applying a strongly cationic quaternized protein and either an anionic latex or an amphoteric polymer to the skin or nails, wherein:

the anionic functional groups of said anionic latex are produced either by polymerization or copolymerization of anionic monomers in which polymerization or copolymerization is effected either by combination of an anionic free radical originating from the reaction initiator with the monomer or the monomers during the initiation of polymerisation of said monomers or by juxtaposition of these two processes of synthesis or, alternatively, by the introduction of end groups by a chain transfer reaction in the second process employing a reaction initiator;

said strongly cationic quaternized protein has the formula:

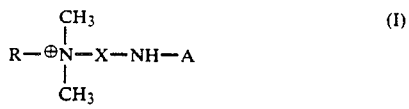

in which A is a protein residue derived from hydrolysates of collagen protein, R is a lipophilic group containing up to 30 carbon atoms, and X is an alkylene group containing from 1 to 6 carbon atoms;

said amphoteric polymer contains two moieties, moiety A and moiety B, which are distributed statistically in said amphoteric polymer chain such that moiety A is derived from a monomer that contains at least one basic nitrogen atom and moiety B is derived from an acidic monomer that contains at least one carboxylic or sulphonic group or moieties A and B are groups that are derived from zwitterionic monomers of carboxybetaines or are cationic polymer chains that contain secondary, tertiary or quaternary amine groups such that at least one of said amine groups includes a carboxylic or sulphonic group connected to said amine group via a hydrocarbon radical, or moieties A and B form part of a chain of a polymer that contains an $\alpha,\beta$-ethylenedicarboxylate moiety in which one of the carboxylic groups has reacted with a polyamine that contains one or more primary, secondary, or tertiary amine groups; and the concentration of said strongly cationic quaternized protein and said anionic latex or amphoteric polymer is between 0.01 and 10% by weight.

17. The process of claim 16, wherein said strongly quaternized protein and either said anionic latex or said amphoteric polymer are applied in a single composition.

18. The process of claim 16, wherein the anionic functional groups of the anionic latex are produced by polymerization of a monomer selected from the group consisting of styrene, butadiene, acrylonitrile, chloroprene, vinylidene chloride, isoprene, isobutylene, vinyl chloride and esters of acrylic, methacrylic, vinyl acetic, maleic, crotonic, or itaconic acid, wherein said monomer is polymerized alone or as a mixture with one or more of the ion-forming monomers selected from the group consisting of acrylic, methacrylic, itaconic, maleic, crotonic, para-styrenesulphonic, vinylsulphonic, 2-methacryloyloxyethylsulphonic and 2-acrylamido-2-methylpropylsulphonic acids.

* * * * *